United States Patent [19]

Ofenloch-Hähnle et al.

[11] Patent Number: 5,212,063

[45] Date of Patent: May 18, 1993

[54] LIGAND TRAP USEFUL IN IMMUNOASSAYS OF BIOTIN OR FREE BIOTIN CONTAINING SAMPLES AND IMPROVED IMMUNOASSAYS USING THESE LIGAND TRAPS

[75] Inventors: Beatus Ofenloch-Hähnle, Munich; Michael Berger, Penzberg; Arno Deger, Seeshaupt, all of Fed. Rep. of Germany

[73] Assignee: Boehringer Mannheim GmbH, Mannheim, Fed. Rep. of Germany

[21] Appl. No.: 521,121

[22] Filed: May 9, 1990

[30] Foreign Application Priority Data

May 9, 1989 [DE] Fed. Rep. of Germany ....... 3915135

[51] Int. Cl.$^5$ .................... C12Q 1/00; G01N 33/544; G01N 33/543; G01N 33/566
[52] U.S. Cl. .................................. 435/7.5; 435/4.92; 435/962; 436/53; 436/512; 436/535; 436/175
[58] Field of Search ............... 435/7.5, 7.9, 6, 962; 436/528, 533, 535, 518, 823, 824, 825, 175

[56] References Cited

U.S. PATENT DOCUMENTS

| | | | |
|---|---|---|---|
| 3,951,748 | 4/1976 | Devlin et al. | 195/103.5 R |
| 4,282,287 | 8/1981 | Giese | 428/407 |
| 4,550,075 | 10/1985 | Bacquet et al. | 435/7 |
| 4,680,274 | 7/1987 | Sakai et al. | 436/512 |
| 4,752,638 | 6/1988 | Nowinski et al. | 525/54.1 |

FOREIGN PATENT DOCUMENTS

| | | |
|---|---|---|
| 0138297 | 4/1985 | European Pat. Off. . |
| 0269092 | 1/1988 | European Pat. Off. . |
| 0353895 | 2/1990 | European Pat. Off. . |
| 0356964 | 3/1990 | European Pat. Off. . |
| 2624613 | 6/1989 | France . |

OTHER PUBLICATIONS

Bier et al. "Fundamentals of Immunology" 2nd Ed. 1986 Springer Verlag, pp. 85, 88.

*Primary Examiner*—David Saunders
*Assistant Examiner*—Nancy J. Parsons
*Attorney, Agent, or Firm*—Felfe & Lynch

[57] ABSTRACT

The present invention provides a process for the detection of analytes in body fluids containing free biotin by immunoassay with the use of biotin conjugates for the labelling, immobilization or complexing of immunological reagents, wherein the biotin present in free form is removed from the immunological reaction by incubating the sample solution with polymer particles consisting of a core and a covering which, as core, contain a polymer which has a plurality of binding sites for biotin and, as covering, at least one layer of protein, peptide, carbohydrate or co-polymer of carbohydrate and amino acids, the layer thickness of the covering being so adjusted that the coating is permeable for the free biotin but not for the biotin conjugate.

9 Claims, 1 Drawing Sheet

LIGAND TRAP USEFUL IN IMMUNOASSAYS OF BIOTIN OR FREE BIOTIN CONTAINING SAMPLES AND IMPROVED IMMUNOASSAYS USING THESE LIGAND TRAPS

The present invention is concerned with a process for the detection of specifically-bindable substances in body fluids according to the immunoassay principle with the use of ligand conjugates for the labelling, immobilisation or complexing which contain in free form the ligands used for the ligand conjugates.

In clinical diagnosis, a plurality of tests are carried out for the detection of specifically-bindable substances in body fluids. Many determinations are based on the principle of homogeneous or heterogeneous immunoassay in which case, as a rule, at least two receptors are used, one of which is labelled and the other of which is immobilised or can be immobilised. Recently, for the labelled or immobilised or immobilisable receptors, conjugates have frequently been used in which the binding of the immune partner specifically bindable with the substance to be determined to the labelling or to the solid phase takes place via the exchange interaction between a ligand and a binding partner specific for this ligand. As a rule, the ligand is a comparatively small molecule, for example a hapten. Since the binding force between biotin and streptavidin or avidin displays one of the highest constants for biological molecules, biotin is very frequently used as ligand and streptavidin as specific binding partner therefor. Besides the many advantages which the use of this pair brings, it has the disadvantage that biotin is a molecule occurring ubiquitously in body fluids. Therefore, if biotin is present in the sample solutions in free form, it occupies binding sites and can, therefore, lead to false results of the test. This is especially critical in the case of patients who received highly dosed amounts of biotin. It is assumed that biotin in an amount of more than 30 ng./ml. of sample already results in falsified results. In the case of patients treated with biotin, serum values of up to 180 ng./ml. and long-lasting values of about 70 ng./ml. can occur. Therefore, a method is required to remove the biotin so that a disturbance of the test does not take place. The same problem arises when other haptens, for example digoxigenin, are used as ligand, which, at the same time, are used therapeutically and, therefore, can also be present in body fluids and there bring about disturbance.

Therefore, it is an object of the present invention to provide a process for the detection of substances in body fluids which contain disturbing ligands in order to capture these ligands so that the detection process is not disturbed.

Thus, according to the present invention, there is provided a process for the detection of specifically-bindable substances in body fluids according to the immunoassay principle with the use of ligand conjugates for the label, immobilising or complexing which contain in free form the ligands used for the ligand conjugates, wherein the ligands present in free form are removed from the immunological reaction by incubating the sample solution with polymer particles consisting of a core and a covering which, as core, contain a polymer which has a plurality of binding positions for the ligands and, as covering, at least one layer of protein, peptide, nucleic acid polymer, polyamide, carbohydrate and/or aggregate of carbohydrate and amino acids, the layer thickness of the covering being so adjusted that the coating is permeable for the free ligands but not for the ligand conjugate.

Surprisingly, with the polymer particles used according to the present invention, it is possible to remove the disturbing ligands from the solution. The polymer particles are so constructed that only free ligands can be bound but not a ligand conjugate, the molecular weight of which is at least twice that of the ligand. In this way, it is possible, also in the case of sample solutions highly loaded with free ligands, to remove the disturbance due to the ligands without having a negative influence on the function of the ligand conjugate in the test system.

The removal of the free ligands carried out according to the present invention takes place for all variants of detection processes according to the immunoassay principle in which a ligand conjugate is used for the labelling, immobilisation or complexing. Ligand refers to a member of a specifically-binding pair which has a relatively low molecular weight and is used in the form of conjugates with labels, for example enzymes or fluorescing substances, or is bound to an antibody or a fragment thereof, for the binding of the antibody to the solid phase. As a rule, the term "ligand" includes low molecular weight antigens, as well as antibodies or fragments thereof. Examples include biotin and digoxigenin. The ligand does not cross-react with either the substance to be detected or with the receptor.

Examples of detection processes in which the principle according to the present invention can be used include sandwich tests and competitive tests in the 1-step process in which, on a solid phase, partners of a specific binding system are immobilised and the substance to be detected is incubated with a labelled receptor, as well as an unlabelled receptor conjugate which contains the other binding partner. The complex formed from the substance to be determined, labelled receptor and receptor with binding partner then binds, on the basis of the specific bindability, to the other partner which is immobilised on the solid phase so that, in this way, the whole complex is immobilised. After separation of the phases, the labelling can then be measured in one of the two phases.

In order to remove the disturbing ligands present in free form, the sample solution is incubated with polymer particles which specifically bind the free form of the ligand and which consist of a core and a covering.

The core provides the binding sites for the ligands and the covering forms a barrier for the separation of the ligands from the ligand conjugates.

In a preferred embodiment, the polymer particles are water-soluble and are present in the incubation solution which contains sample and reagents.

The core has a plurality of binding sites for the ligands. It can be either a homogeneous polymer or a heterogenous polymer of substances bindable with the ligands or, can consist of an inert core and a covering of bindable substances. Inert, as used herein refer to substances which are inert with regard to the immunological reaction and the detection reaction.

The binding positions in the core for the ligands are provided by a substance specifically bindable with the ligands. This specifically-bindable substance can be the other partner of a specifically-binding pair and can be identical with the partner used for the binding of the ligands which are present in immobilised or labelled form. Examples of appropriate binding pairs include biotin-avidin, biotin-streptavidin, antigen-antibody, hapten-antibody, protein A-immune-γ-globulin, protein G-immune-γ-globulin, as well as hapten-binding protein and also the particular bindable derivatives. The polymer of the substances bindable with the ligand can be produced by cross-linking of the individual binding partners with one another or with an inert molecule. The individual binding partners can be bound with one another via homo- or heterobi- or polyvalent linkers. The cross-linking is preferably carried out with bivalent linkers since this makes easier control of the degree of polymerisation possible. However, polyvalent linkers can also be used. As linkers, those compounds which have reactive groups which, in aqueous solution, are able to react with the functional groups of the specifically-bindable partner with the formation of a covalent bond are used. A large number of bifunctional and polyfunctional linkers are known for this purpose. Typical examples of appropriate homo- or hetero-bifunctional and trifunctional linkers which can well be used in the scope of the present invention are set out in the following Table 1:

TABLE 1

| abbreviation | chemical designation |
|---|---|
| SPDP | N-succinimidyl 3-(2-pyridyldithio)-propionate |
| EADB | ethyl 4-azidophenyl-1,4-dithiobutyrimidate · HCl |
| FNPA | 4-fluoro-3-nitrophenylazide |
| HSAB | N-hydroxysuccinimidyl-4-azidobenzoate |
| MABI | methyl-4-azidobenzoimidate · HCl |
| MBS | m-maleimidobenzoyl-N-hydroxysuccinimide ester |
| NHS-ASA | N-hydroxysuccinimidyl-4-azidosalicylic acid |
| MHS | maleimidohexanoyl-N-hydroxysuccinimide ester |
| PNP-DTP | p-nitrophenyl-2-diazo-3,3,3-trifluoro-propionate |
| SADP | N-succinimidyl-(4-azidophenyl)-1,3'-dithiopropionate |
| SAND | sulphosuccinimidyl-2-(m-azido-o-nitro-benzamido)-ethyl-1,3'-dithiopropionate |
| SANPAH | N-succinimidyl-6-(4'-azido-2'-nitro-phenylamino)-hexanoate |
| SASD | sulphosuccinimidyl-2-(p-azidosalicyl-amido)-ethyl-1,3'-dithiopropionate |
| SIAB | N-succinimidyl (4-iodoacetyl)-amino-benzoate |
| SMCC | succinimidyl-4-(N-maleinimidoethyl) cyclohexane-1-carboxylate |
| SMPB | succinimidyl 4-(p-maleimidophenyl)-butyrate |
| DSS | disuccinimidyl suberate |
| DMS | dimethyl suberimidate |
| Traut's reagent | 2-iminothiolane 2,4,6-trichloro-s-triazine |
| SAMBA | S'-acetylmercaptosuccinic acid anhydride |
| SATA | N-succinimidyl-S-acetylthioacetate |

For carrying out the cross-linking, a solution of the binding partner can be mixed with the linker molecules under conditions which lead directly to the cross-linking. The extent of the cross-linking is, in this case, controlled by the amount of added linker. In a further preferred embodiment, the binding partner is cross-linked with appropriate bindable components which are inert with regard to the ligands and to the compound to be determined. For this purpose, there can be used, for example, a soluble protein and especially bovine serum albumin or human serum albumin.

The core can consist entirely of the polymer of the binding partner. It can also have an inert core which can consist, for example, of polystyrene or dextran and is covered with the polymer of the substance bindable with the ligands.

In the case of the most frequently used ligand biotin, a polymer of antibiotin antibodies is used for the core polymer or, especially preferred embodiment a polymer of avidin or streptavidin. In the case of the use of digoxigenin as ligand, the core polymer preferably contains anti-digoxigenin antibody or fragments thereof. If streptavidin or avidin is the ligand, then the core polymer contains biotin molecules or derivatives thereof bindable with streptavidin or avidin, for example iminobiotin or biocytin.

The core is covered by a coating which is so formed that the coating is permeable for the free ligands but not for the ligand label conjugate. The covering consists of at least one layer of protein, peptide, nucleic acid polymer, carbohydrate, polyamide and/or a aggregate of carbohydrate and amino acids. These components can also be used in derivatised form.

The size of the core is itself not critical and is essentially limited by the solubility of the particles of the given molecular weight. For binding of the ligands occurring in free form, a sufficient number of binding positions in the core is necessary. It has been found that a few binding positions in the core already bring about a noticeable removal of disturbances. Good removal of disturbances takes place when anywhere from about 10 binding positions per particle are available and especially good removal of disturbances occurs when anywhere from about 50 binding positions or more per particle are available.

For the formation of the coating, it is preferred to use polymeric bovine serum albumin, polymeric Fab fragments or aminodextran polymer. The production of the polymers takes place according to known method by cross-linking of the individual components. The layer thickness is thereby so adjusted that the coating is permeable for the free ligands but not for the ligand conjugate.

The core polymer is covered with at least one layer. The coating is preferably made up of at least two layers which can be the same or different. The covering preferably has a spongy or absorbent structure which makes especially well a selective permeability possible. This happens, for example, in the case of multiple covering with bovine serum albumin and/or Fab' fragments of antibodies.

The coating can take place covalently, adsorptively or by binding via a specific binding pair (for example biotin/avidin) as functional linking.

With the process according to the present invention, it is possible to remove disturbing ligands from the sample solution. The removal of disturbances takes place up into high ranges of concentration. Thus, it is possible to remove the biotin almost completely from sample solutions which contain up to 200 ng./ml. of biotin. In the case of still higher loaded samples, at least substantial removal is possible. Thus, the process according to the present invention makes possible an improvement of the exactitude and reproduceability of determinations according to the immunoassay principle.

The present invention also provides a ligand trap consisting of a water-soluble, polymeric receptor molecule which contains a core and a covering, in which the core is a polymer which has a plurality of binding sites for the ligands and the covering consists of at least one layer of protein, peptide, nucleic acid polymer, carbohydrate, polyamids and/or aggregate of carbohydrate and amino acids, the layer thickness of the covering being such that the covering is permeable for the ligand but not for the ligand conjugate.

BRIEF DESCRIPTION OF THE FIGURES

FIG. 2a shows an embodiment in which, on a solid phase 11, an antibody 13 is immobilized which is bindable with the substance 15 to be determined. The sample solution which contains the substance 15 to be determined is incubated with a receptor 17 which is bindable with the substance 15 to be determined and is conjugated with biotin. Furthermore, a conjugate 19 of a label and streptavidin is present in the sample solution, Receptor 17 reacts with the substance 15 to be determined and is immobilised on the solid phase via the antibody 13 which binds to the substance 15. The label is bound via the streptavidin contained in the receptor 19 and the biotin contained in the receptor 17;

FIG. 2b shows, a further variation, i.e. a competitive process. An antibody 13 bindable with the substance to be determined is immobilized on the solid phase II. A conjugate 14 which consists of the substance to be determined and biotin, as well as a conjugate of a label and streptavidin are added to the sample solution. In the case of the immunological reaction, the substance 18 to be determined and biotin-containing conjugate 14 compete for the binding to the solid phase-bound antibody. The binding of the label takes place, via the streptavidin contained in the labelled receptor, to the biotin-containing conjugate.

EXAMPLE 1

Preparation of polystreptavidin (SA(P))

a) Preparation of maleiniminohexanoylstreptavidin (SA-MH)

Figure 1A:
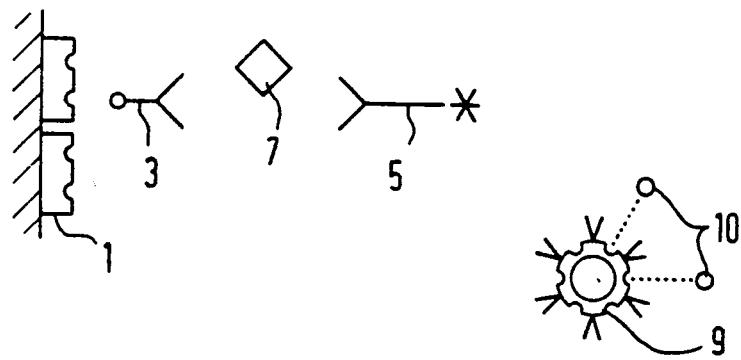
FIG. 1a shows a preferred embodiment of the process according to the present invention; here, a solid phase 1, on which streptavidin is immobilised, is incubated with a receptor 3 which is bindable with the substance 7 to be determined and is conjugated with biotin, as well as with a labelled receptor 5 which is bindable with the substance 7 to be determined, together with the substance containing sample solution. Furthermore, the solution contains the ligand trap 9 according to the present invention. The analyte 7, to which the labelled receptor 5 is bound, binds via the receptor 3 to the solid phase 1. Biotin 10 present in the solution reacts with the ligand trap 9 and does not enter into the immunological reaction.
Figure 1B:
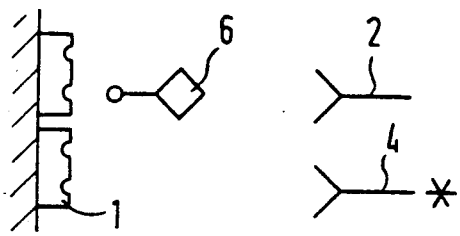
FIG. 1b shows a variation of the competitive immunoassay. Streptavidin is bound to a solid phase 1. The solid phase is incubated with the antibody 2 to be determined, as well as with an antibody 4, analogous to the antibody to be determined, which carries a label and, furthermore, an antigen 6, bindable with analyte and labelled receptor, which is conjugated with biotin. In the case of the reaction, antibody 2 to be determined and labelled receptor 4 compete for the binding to the antigen 6. The complexes formed from antibody and antigen bind via biotin to the solid phase coated with streptavidin.
Figure 2A:
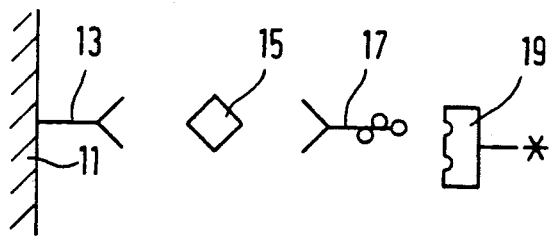
FIGS. 2a and 2b show further variants of the process according to the present invention.
Figure 2B:
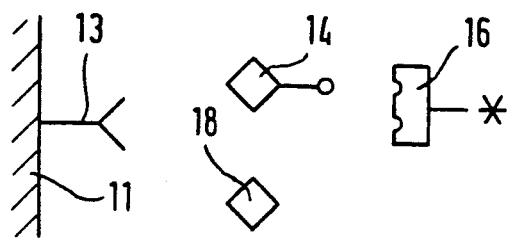

500 mg. Streptavidin were dissolved in 50 ml. 50 mmole/liter potassium phosphate buffer (KPB) and 100 mmole/liter sodium chloride (pH 6.6) and incubated for 2 hours at 4° C. with 25 mg. maleinimidohexanoyl-N-hydroxysuccinimide ester (MHS) which had previously been dissolved in dimethyl sulphoxide. Thereafter, dialysis was carried out against 10 mmol/liter KPB/50 mmole/liter sodium chloride (pH 6.2).

b) Preparation of SAMBA-derivatised streptavidin (SA-SAMB)

A further 500 mg. streptavidin were dissolved in 50 mmole/liter KPB/100 mmole/liter sodium chloride (pH 7.8), mixed with 29 mg. SAMBA predissolved in dimethyl sulphoxide and incubated, while stirring, for 3.5 hours at 25° C. Thereafter, the reaction mixture was dialysed against 50 mmole/liter KPB/100 mmole/liter sodium chloride/1 mmole/liter ethylenediamine-tetraacetic acid (EDTA) (pH 6.0).

c) Coupling of SA-MH and SA-SAMB 50 ml. of the dialysed SA-SAMB solution were mixed with 275 pl. 1/mole/liter hydroxylamine solution and incubated for 30 minutes at 25° C. Thereafter, the reaction mixture was dialysed twice against, in each case, 2 liters 50 mmole/liter KPB/100 mole/liter sodium chloride/2 mmole/liter EDTA (pH 6.5). The dialysate was mixed with 110 ml. of the dialysis buffer and 55 ml. of the dialysed SA-MH solution added thereto. The mixture was incubated for 2 to 4 hours at 25° C., while stirring, and the degree of cross-linking was tested at half hour intervals by means of FPLC gel filtration. If an average apparent molecular weight of 700 to 800 kD has been achieved, the cross-linking was stopped by the addition of cysteine (ad 1 mmole/liter, 30 minutes, 25° C.) and of iodoacetamide (ad 5 mmole/liter, 30 minutes, 25° C.). The streptavidin polymer obtained (SA(P)) was purified by gel filtration on Superose 6 in 50 mmole/liter KPB/100 mmole/liter sodium chloride/1% saccharose (pH 6.8).

The SA(P)-containing fractions were collected, concentrated by means of ultrafiltration to c=5 mg./ml., made up with saccharose to 80 mg./ml. and lyophilised.

EXAMPLE 2

Preparation of polymer particles, the core of which consists of a streptavidin polymer and the covering of which consists of two layers of bovine serum albumin (BSA)

SA(P) lyophilisate prepared as described in Example 1 was dissolved in water to 25 mg./ml. and the pH value was adjusted to 7.0. 2 ml. of the SA(P) solution obtained were mixed with 2.6 mg. MHS, predissolved in dimethyl sulphoxide, and incubated, while stirring, for 60 minutes at 25° C. After the addition of 20 μl. 1 mole/liter lysine, dialysis was carried out against 10 mmole/liter KPB/100 mmole/liter sodium chloride/2 mmole/liter EDTA (pH 6.2). The dialysate was mixed with 5 ml. BSA solution (100 mg./ml. BSA in 10 mmole/liter KPB/100 mmole/liter sodium chloride/2 mmole/liter EDTA (pH 6.9); BSA:SA(P)=10:1 mg./mg.), the pH of the reaction mixture was adjusted to 6.9 and incubated for 2 hours at 25° C. After the addition of 44 μl. 0.2 mole/liter cysteine solution, BSA-SA(P) was purified from unreacted BSA by means of gel filtration on acrylamide agarose. 7.5 mg. of the BSA-SA(P) obtained in this way in 1.95 ml. 50 mmole/liter KPB/100 mmole/liter sodium chloride/2% saccharose (pH 7.0) were mixed with 770 μg. MHS, predissolved in dimethyl sulphoxide, and incubated for 1 hour at 25° C. Thereafter, 20 μl. 1 mmole/liter lysine were added thereto, followed by dialysis against 10 mmole/liter KPB/100 mmole/liter sodium chloride/2 mmole/liter EDTA (pH 6.2). 1.76 ml. of the dialysate (=5 mg.BSA-SA(P), MH-activated) was mixed with 1.1 ml. of the above-described BSA solution, the pH was adjusted to 6.9 and incubated at 25° C. (BSA:BSA-SA(P)=10:1 mg./mg.). Thereafter, 29 μl. of a 0.2 mmole/liter cysteine solution were added thereto, followed by incubation for 30 minutes at 25° C. The BSA-BSA-SA(P) obtained was separated from unreacted BSA by means of gel filtration (AcA 22, 50 mmole/liter KPB/100 mmole/liter sodium chloride/2% saccharose (pH 7.5)). The fractions containing BSA-BSA-SA(P) were collected and concentrated by ultra-filtration to a concentration of about 1 mg./ml.

EXAMPLE 3

Preparation of polymer particles, the core of which consists of a streptavidin polymer and the covering consists of two sequentially applied layers of Fab' fragment The procedure was analogous to that described in Example 2 but, instead of BSA, there were used Fab' fragments of a monoclonal anti-TSH-antibody. Fab' and SA(P) or Fab' and Fab'-SA(P) were thereby used in a ratio of 5:1 mg./ml. Otherwise the reaction conditions were identical.

The hybridoma cell line which produces the anti-TSH antibodies has been deposited at the European Collection of Animal Cell Cultures in Great Britain under the designation ECACC 87122202.

EXAMPLE 4

Preparation of polymer particles, the core of which consists of streptavidin polymer and the covering of which consists of aminodextran.

In the manner described in Example 2, SA(P) was reacted with MHS and subsequently dialysed against 50 mmole/liter KPB/100 mmole/liter sodium chloride/2 mmole/liter EDTA (pH 6.2).

250 mg. Aminodextran (M.W. 20,000) were dissolved in 10 ml. 100 mmole/liter KPB (pH 7.3). Thereafter, 2.9 mg. SATA, predissolved in dimethyl sulphoxide, were added thereto, followed by incubation for 1 hour at 25° C. After the addition of a 1 mole/liter lysine solution to 10 mmole/liter, the pH of the reaction mixture was adjusted to 6.3, followed by dialysis against 50 mmole/liter KPB/100 mmole/liter sodium chloride/2 mmole/liter EDTA (pH 6.2). 1 mole/liter hydroxylamine (pH 6.2) was added to the dialysate, followed by incubation for 30 minutes at 25° C. Thereafter, the reaction mixture was dialysed twice for one hour against, in each case, 1 liter 50 mmole/liter KPB/100 mmole/liter sodium chloride/2 mmole/liter EDTA (pH 6.2). The dialysate was mixed with 10 ml. SA(P)-MH solution in dialysis buffer (c=1 mg./mk.), the pH was immediately adjusted to 6.9 and then incubated for 1 hour at 25° C. Subsequently, cysteine was added to 1 mmole/liter, followed by incubation for 30 minutes at 25° C. Thereafter, iodoacetamide was added to 5 mmole/liter, again followed by incubation at 25° C. for 30 minutes. The aminodextran-streptavidin co-polymer obtained was evaporated and separated from unreacted aminodextran by means of gel filtration (acrylamide agarose, 50 mmole/liter KPB/100 mmole/liter sodium chloride/2% saccharose (pH 7.5)). The aminodextran-streptavidin co-polymer-containing fractions were combined and concentrated by ultra filtration to a concentration of about 1 mg./ml.

EXAMPLE 5

Removal of biotin disturbance in the CEA test (test for carcinoembrionic antigen) by Fab'-Fab'-SA(P)

Test Preparation

CEA-containing horse serum (50 ng. CEA/ml.) was made up with 50, 100 and 200 ng./ml. biotin. The reagent solution, containing a conjugate of Fab fragments of monoclonal antibodies (IgG) against CEA with peroxidase (POD), as well as biotinylated monoclonal antibody (IgG) against CEA in 50 mmole/liter 2-(N-morpholino)-ethanesulphonic acid buffer (pH 6.1), was made up with 5 or 7 μg./ml. Fab'-Fab'-SA(P) (prepared as described in Example 3).

The test was carried out according to the procedure of the commercially available test kit Enzymun $^R$ CEA (Boehringer Mannheim GmbH, Order No. 1132814).

Carrying out of the test

100 μl. of CEA-containing horse serum, together with 1 ml. of the reagent solution, which contained peroxidase-labelled monoclonal anti-CEA antibody (20 mU POD/ml.) and biotin-labelled monoclonal CEA antibody (1.5 μg./ml.), were pipetted into a Luran test tube coated with streptavidin and incubated for 2 hours at 25° C. There was thereby formed a complex of peroxidase-labelled CEA antibody, CEA and biotin-labelled CEA antibody, CEA and biotin-labelled CEA antibody which was immobilised by binding of the biotin to the streptavidin bound to the solid phase. The content of the test tube was thereafter sucked out, the test tube was rinsed three times and again carefully sucked out. Thereafter, the proportion of peroxidase activity was determined by the addition of 1 ml. of a substrate solution which contained 1.9 mmole/liter ATBS$^R$ solution (2,2'-azino-di-[3-ethylbenzthiazoline-6-sulphonate] in 100 mmole/liter phosphatecitrate buffer/3.2 mmole/liter sodium perborate (pH 4.4) and incubated for 1 hour at 25° C. The extinction with the sample was then measured at 405 nm against the extinction of the substrate chromogen solution as blank.

Results

As shown in the following Table 2, by means of the addition of Fab'-Fab'-SA(P), the biotin disturbance in this test system could be quantitatively removed up to 100 ng./ml. of biotin in the sample and, in the case of higher biotin concentrations, was distinctly reduced.

TABLE 2

| biotin addition | % of the initial value[1] | | |
|---|---|---|---|
| ng/ml. | without polymer | 5 μg/ml polymer | 7 μg/ml polymer |
| 0 | 100 | 92 | 85 |
| 50 | 78 | 92 | 84 |
| 100 | 46 | 85 | 82 |
| 200 | 20 | 43 | 60 |

[1]initial value: extinction (less blank) with sample without biotin and without addition of polymer particles.

EXAMPLE 6

Removal of the biotin disturbance in a test for the detection of anti-HBc antibodies (antibodies against hepatitis B core antigen; European Patent Specification No. B-0,013,828) by BSA-BSA-SA(P).

Test preparation

Anti-HBc antibody-free serum was made up with 50, 100 and 200 ng./ml. of biotin. A solution containing an HBc-antigen (HBcAg)-biotin conjugate (prepared by the reaction of HBcAg with N-hydroxysuccinimide-activated biotin) in 40 mmole/liter phosphate buffer (pH 7.4) was made up with BSA-BSA-SA(P), which was prepared as described in Example 2, to 7.5 to 12.5 μg./ml.

Carrying out of the test

The determination was carried out in a 2-step assay according to the competition principle. As solid phase, there were used synthetic material test tubes coated with thermo-BSA-streptavidin (prepared according to published European Patent Specification No. A-0,269,092). As labelled receptors, there were used anti-HBc antibody-peroxidase conjugates.

200 μl. of a serum free of anti-HBc antibodies, together with 1 ml. of a solution which contains biotin-HBcAg conjugate (10 ng./ml.), were pipetted into Luran test tubes coated with thermo-BSA-streptavidin and incubated for 1 hour at 25° C. The anti-HBc antibodies from the sample thereby reacted with the biotin-HBcAg conjugate and complexes formed were immobilised by binding of the biotin from the conjugate on to the solid phase-bound streptavidin. Thereafter, the contents of the test tubes were sucked out and the test tubes were washed three times with water. Non-bound biotinylated HBcAg and all serum components were thereby removed. Subsequently, 1 ml. of a solution which contained peroxidase-labelled anti-HBcAg antibody (200 mU peroxidase/ml.) was added thereto and incubated for 1 hour at 25° C. Peroxidase-labelled anti-HBc antibodies thereby bound with antigen binding positions not occupied by the sample. Subsequently, the contents of the test tubes were sucked out and the test tubes again washed three times, non-bound peroxidase conjugate thereby being removed. Thereafter, 1 ml. of 1.9 mmole/liter ABTS solution in 100 mmole/liter phosphatecitrate buffer/3.2 mmole/liter sodium perborate (pH 4.4) was added thereto, followed by incubation for 1 hour at 25° C. Subsequently, the extinction with sample was determined at 405 nm against the extinction of the substrate chromogen solution (blank).

As the following Table 3 shows, by means of the addition of BSA-BSA-SA(P) to this test system, the biotin disturbance can be almost completely removed up to 200 ng./ml.

TABLE 3

| biotin addition ng/ml. | % of the initial value[1] | | | |
|---|---|---|---|---|
| | without polymer | 7.5 μg/ml polymer | 10 μg/ml polymer | 12.5 μg/ml polymer |
| 0 | 100 | 93 | 90 | 89 |
| 50 | 74 | 93 | 90 | 87 |
| 100 | 50 | 91 | 86 | 85 |
| 200 | 24 | 55 | 70 | 78 |

[1]initial value: extinction (less blank) with sample without biotin and without addition of polymer particles.

EXAMPLE 7

Preparation of polymer particles, the core of which consists of bovine serum albumin-streptavidin copolymer and the covering of which consists of Fab' fragments Analogously to Example 2, BSA-SA(P) was first prepared. This co-polymer was activated with MHS as described in Example 2. The BSA-SA(P)-MH was reacted with Fab fragments of anti-TSH antibodies (cf. Example 3) in a ratio of 5:1 mg./mg. under the reaction conditions described in Example 2.

EXAMPLE 8

Removal of biotin disturbance in a test for the detection of anti-HBc antibodies by Fab'-BSA-SA(P)

The test was carried out as described in Example 6 but the HBcAg-biotin solution was made up with 10 and 15 μg./ml. Fab'-BSA-SA(P). Serum and HBcAg-biotin solution were not pipetted together into the streptavidin-coated Luran test tubes but rather 200 μl. of serum were first added to the test tubes and only after a time interval of 2 to 5 minutes was the HBcAg-biotin conjugated solution added thereto.

The following Table 4 shows that, in the case of this changed carrying out of the test, a distinct removal of the disturbance is also to be observed.

TABLE 4

| biotin addition ng/ml. | % of the initial value[1] | | |
|---|---|---|---|
| | without polymer | 10 μg/ml polymer | 15 μg/ml polymer |
| 0 | 100 | 85 | 80 |
| 100 | 52 | 74 | 69 |
| 200 | 28 | 50 | 67 |

[1]initial value: extinction (less blank) with sample without biotin and without addition of polymer particles.

We claim:

1. In an immunoassay for determining an analyte in a body fluid sample, wherein said sample is contacted with a conjugate of biotin and a receptor for said analyte and any complexes formed between said conjugate and analyte are determined, and wherein said sample contains in addition to said analyte, free biotin or a derivative of free biotin, the improvement comprising adding to said body fluid sample a water soluble, polymeric particle consisting of:
   (a) a polymer core having at least 10 binding sites for said free biotin or derivative of free biotin, and
   (b) a coating on said polymer core, wherein said coating is at least one layer in thickness and comprises a protein, a peptide, a carbohydrate or a aggregate of carbohydrate and amino acids, wherein said coating is permeable to said free biotin or said derivative of free biotin but not said conjugate of biotin and receptor for said analyte.

2. The immunoassay of claim 1, wherein said coating is at least two layers in thickness.

3. The immunoassay of claim 2, wherein said at least two layers are different from each other.

4. The immunoassay of claim 1, wherein said coating comprises polymeric bovine serum albumin, a polymer of antibody Fab fragments, or an aminodextran polymer.

5. The immunoassay of claim 1, wherein said polymer core comprises a polymer of (i) a specifically bindable substance for said free biotin or derivative of free biotin, and (ii) an immunologically inert material.

6. The immunoassay of claim 1, wherein said polymer core comprises homogenously cross linked polymeric avidin, homogeneously cross linked polymeric streptavidin, heterogeneously cross linked polymeric avidin, or heterogeneously cross linked polymeric streptavidin.

7. Ligand trap consisting essentially of:
(a) a water soluble polymer core having at least 10 binding sites for free biotin or a derivative of free biotin, the polymer of said core being selected from the group consisting of a polymer of biotin specific antibody, a polymer of avidin and a polymer of streptavidin, and
(b) a coating of at least one layer thickness, wherein said coating comprises a protein, a peptide, a carbohydrate or a aggregate of carbohydrate and amino acids, wherein said coating is permeable to free biotin or a derivative of free biotin but not to a conjugate of biotin and receptor.

8. The ligand trap of claim 7, wherein said polymer core further comprises polystyrene or dextran.

9. The ligand trap of claim 7, wherein said coating comprises polymeric bovine serum albumin, a polymer of antibody Fab fragments, or an aminodextran polymer.

* * * * *